United States Patent
Peralta Uroz et al.

(10) Patent No.: US 10,336,977 B2
(45) Date of Patent: Jul. 2, 2019

(54) BIOREACTOR FOR CELL CO-CULTURE

(71) Applicants: INSTITUT D'INVESTIGACIONS BIOMEDIQUES AUGUST PI I SUNYER (IDIBAPS), Barcelona (ES); CONSEJO SUPERIOR DE INVESTIGACIONES CIENTIFICAS, Madrid (ES); CIBER CENTRO DE INVESTIGATIÓN BIOMÉDICA EN RED, Madrid (ES); HOSPITAL CLÍNIC DE BARCELONA, Barcelona (ES); UNIVERSITAT DE BARCELONA, Barcelona (ES)

(72) Inventors: Carmen Peralta Uroz, Barcelona (ES); Jordi Gracia Sancho, Tarragona (ES); Rosa Villa Sanz, Barcelona (ES); Javier Illa Vila, Barcelona (ES); Marta Massip Salcedo, Barcelona (ES); Jaime Bosch Genover, Barcelona (ES)

(73) Assignees: INSTIT D'INVESTIGACIONS BIOMEDIQUES AUGUST PI I SUNYER (IDIBAPS), Barcelona (ES); CONSEJO SUPERIOR DE INVESTIGACIONES CIENTIFICAS, Madrid (ES); CIBER CENTRO DE INVESTIGATIÓN BIOMÉDICA EN RED, Madrid (ES); HOSPITAL CLINIC DE BARCELONA, Barcelona (ES); UNIVERSITAT DE BARCELONA, Barcelona (ES)

( * ) Notice: Subject to any disclaimer, the term of this patent is extended or adjusted under 35 U.S.C. 154(b) by 312 days.

(21) Appl. No.: 15/120,562

(22) PCT Filed: Mar. 5, 2015

(86) PCT No.: PCT/EP2015/054683
§ 371 (c)(1),
(2) Date: Aug. 22, 2016

(87) PCT Pub. No.: WO2015/128510
PCT Pub. Date: Sep. 3, 2015

(65) Prior Publication Data
US 2017/0009192 A1    Jan. 12, 2017

(30) Foreign Application Priority Data

Feb. 28, 2014  (EP) .................................... 14157145

(51) Int. Cl.
| C12M 1/00 | (2006.01) |
| C12M 1/12 | (2006.01) |
| C12M 1/42 | (2006.01) |

(52) U.S. Cl.
CPC ............ *C12M 25/06* (2013.01); *C12M 23/04* (2013.01); *C12M 23/40* (2013.01); *C12M 25/02* (2013.01);
(Continued)

(58) Field of Classification Search
CPC ...... C12M 25/06; C12M 25/02; C12M 25/04; C12M 29/20; C12M 29/10; C12M 23/40; C12M 35/04
See application file for complete search history.

(56) References Cited

U.S. PATENT DOCUMENTS

2013/0295601 A1* 11/2013 Park .................... G01N 33/5011
435/32

FOREIGN PATENT DOCUMENTS

| DE | 102012200939 | 7/2013 |
| WO | 03/060061 | 7/2003 |

(Continued)

OTHER PUBLICATIONS

International Search Report for PCT/EP2015/054683, dated Mar. 25, 2015.
(Continued)

*Primary Examiner* — Michael L Hobbs
(74) *Attorney, Agent, or Firm* — Staas & Halsey LLP

(57) ABSTRACT

A bioreactor for cell co-culture having at least first and second cell culture chambers which are separated by a porous membrane. The membrane has at least one sealing gasket integrated in the membrane and being integral therewith. The sealing gasket defines a closed perimeter delimiting a first cell culture area.

11 Claims, 12 Drawing Sheets

(52) U.S. Cl.
CPC ............ *C12M 25/04* (2013.01); *C12M 29/10* (2013.01); *C12M 29/20* (2013.01); *C12M 35/04* (2013.01)

(56) References Cited

FOREIGN PATENT DOCUMENTS

| WO | 2004/076608 | 9/2004 | | |
|---|---|---|---|---|
| WO | 2007/021919 | 2/2007 | | |
| WO | 2010/148275 | 12/2010 | | |
| WO | WO-2010148275 A2 * | 12/2010 | ............ | C12M 23/34 |
| WO | 2013/086509 | 6/2013 | | |

OTHER PUBLICATIONS

Written Opinion of the International Searching Authority for PCT/EP2015/054683, dated Mar. 25, 2015.
Thomson Innovation English Abstract for DE 102012200939.
Notification of Decision Granting Request to Restore Right of Priority for PCT/EP2015/054683, dated Feb. 22, 2016.
Request for Restoration of Right of Priority filed in PCT/EP2015/054683, dated Apr. 23, 2015.
Response in corresponding European Patent Application No. 15707975.7, 6 pgs.
International Preliminary Report on Patentability for PCT/EP2015/054683, dated Sep. 6, 2016.
Response to Communication Pursuant to Rules 161(1) and 162 EPC for PCT/EP2015/054683, dated Apr. 6, 2017.

* cited by examiner

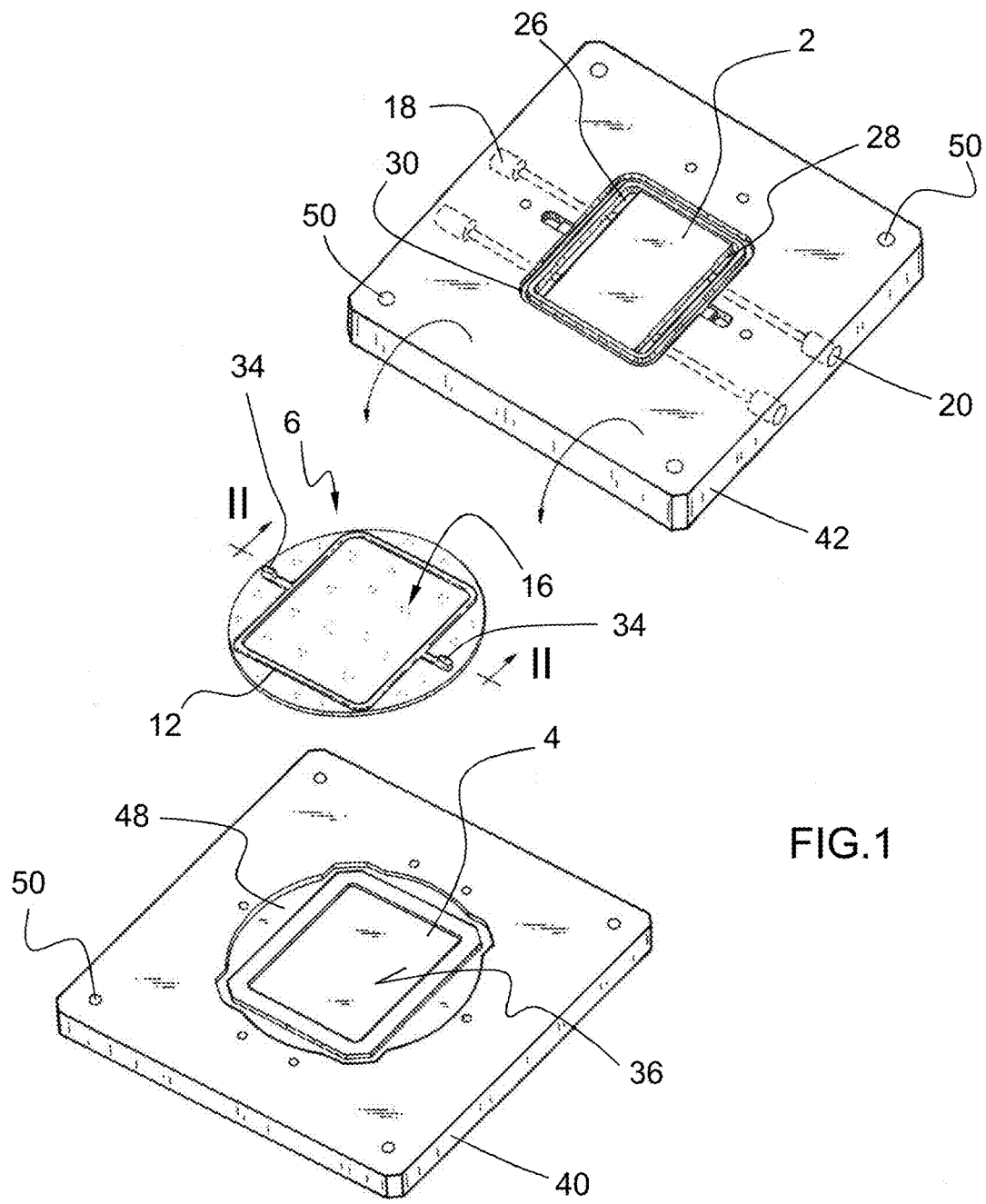
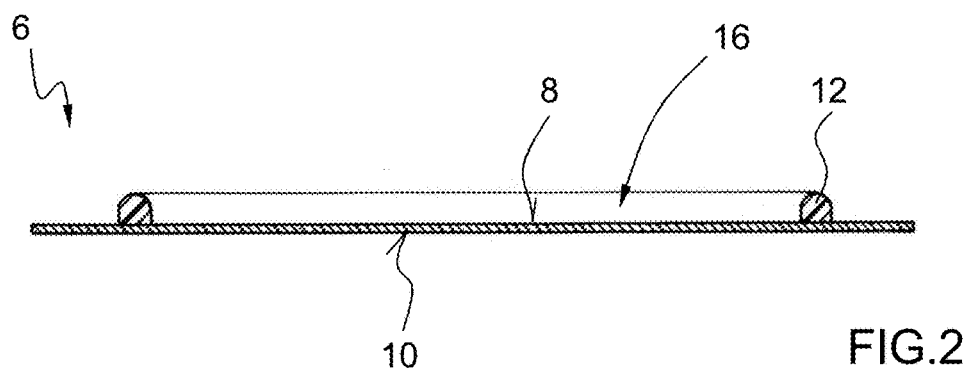
FIG.1
FIG.2

BIOREACTOR FOR CELL CO-CULTURE

CROSS-REFERENCE TO RELATED APPLICATIONS

This application claims the benefit under 35 U.S.C. Section 371, of PCT International Application No. PCT/EP2015/054683, filed Mar. 5, 2015, which claimed priority to European Patent Application No. 14157145.5, filed Feb. 28, 2014, the contents of which are incorporated herein by reference.

DESCRIPTION

Field of the Invention

The invention is located in the technical area of cell engineering and, in particular, in the area of devices for the in vitro culture and growth of various types of cell simultaneously in one same device, a technique regularly called cell co-culture.

More precisely, the invention relates to a bioreactor and a method for cell co-culture.

State of the Art

In the state of the art, bioreactors for cell co-culture having two chambers separated by a permeable membrane are known. One type of cell is seeded in each chamber.

Furthermore, in certain known bioreactors, at least one of the chambers is provided with perfusion fluid inlet and outlet ducts. In this way, cultures may be carried out under both static and dynamic conditions. In the second case, the perfusion fluid flows in a circuit crossing through the bioreactor. The application of the tangential flow on the culture layer is known in the art as shear stress.

These devices allow conditions to be reproduced in vitro similar to those existing in vivo, with the aim of producing tissues, testing drugs by simulating the structure of the blood vessels or other applications in the biotechnological field.

WO 2004/076608 A2 discloses a bioreactor for co-culture allowing static and dynamic culture. The bioreactor is provided with two chambers separated by a membrane. Likewise, thanks to the corresponding perfusion fluid inlet and outlet ducts, the device allows a shear stress type of biomechanical stimulus to be applied to the cells cultured therein.

The membrane of the bioreactor of WO 2004/076608 A2 is a sheet of material suitable for cell culture of a thickness of a few μm (micrometers) which has to be mounted on a metal frame. The handling of the membrane, as well as the assembly thereof in the metal frame is complicated.

If, firstly, the membrane is mounted in the frame and the cells are seeded thereafter, a known working area is available. Nevertheless, it may happen that during the seeding and culture outside the bioreactor the cells may die and therefore the culture is unviable. If the culture is unviable, valuable test time has been lost.

Alternatively, it would be possible to seed previously on the membrane without the metal frame, outside the bioreactor. Nevertheless, this is complicated. This type of membranes is extremely thin, in the order of micrometers. Consequently, the handling thereof is delicate and complicated, since it may easily be creased. On the other hand, once the culture is seeded on the membrane, the situation does not improve much either, due to the aforesaid problem of its low rigidity. Furthermore, in a raw membrane it is difficult to determine the limits of the seeding area. Therefore, owing to the laxness of the membrane and the limits of the seeding area are not known, it is difficult to ensure that the seeded cells are not damaged during assembly of the membrane on the bioreactor frame.

Another known bioreactor also consists of a first and second chambers separated from one another by a porous membrane. Nevertheless, this bioreactor, unlike the previous one, has small dimensions, is integral and cannot be disassembled for accessing the culture chambers. Consequently, access ducts are provided in the bioreactor for accessing the culture chambers. These ducts are used in the first place as access to the culture chambers for seeding the cells. Then, these ducts are used thereafter for applying the shear stress stimulus.

Nevertheless, this bioreactor has the drawback that cell seeding is very complex. Upon supplying the cells through the ducts, many are trapped therein and do not reach the culture chambers. On other occasions, these cells die on the way. This causes the culture preparation to be very laborious and that it is not easy to prepare viable homogenous cultures, with a number of cells suitable for carrying out drug, cell growth tests or the like. Therefore, if it is not wanted to waste testing time, various bioreactors must be cultured in parallel, to guarantee that at least one of them has a viable culture.

A further disadvantage of this device is the impossibility of separately analysing each cell type once the experiment has ended. Likewise, a further disadvantage in this type of bioreactors is that at the end of the corresponding test, the whole bioreactor has to be disposed, namely membrane and housing, which represents a greater financial cost than in the case of the WO 2004/076608 A2 bioreactor.

Document WO 2010/148275 A2 discloses bioreactor systems and methods of utilizing said systems.

Document WO 2007/021919 A1 discloses multi-chambered cell co-culture systems. The systems can be utilized to encourage the growth and development of isolated cells in a dynamic three-dimensional in vitro environment. The cell chambers of the system can be in biochemical communication with adjacent chambers containing cells of different types, but the different cell types are maintained physically separated from one another. In addition, the local environment of each cell chamber can be independently controlled.

Document WO 2013/086509 A1 discloses a flow chamber assembly for subjecting cells or other biological reagents to laminar flow conditions and methods of using the flow chamber assembly are provided herein. The flow chamber assembly includes a bottom plate having at least one well with a bottom surface adapted to receive the cells or biological reagents, a top plate having at least one flow protrusion positioned and shaped to fit into the well of the bottom plate and a sealing element positioned between the top plate and the bottom plate when the top plate and the bottom plate are attached. The flow chamber assembly is configured to allow for laminar flow of a perfusate across the cells or biological reagents along the bottom surface of the well of the bottom plate. The cells or biological reagents can be exposed to a predetermined level of shear stress.

Consequently, the known bioreactors do not offer enough versatility to maximize the viability of the cell cultures, as well as the ease of use of the bioreactor and post-experiment analysis of the cultured cell types.

Definitions

In the invention, the concept of "cell co-culture" does not refer exclusively to the culture of two differentiated cell types, but refers to the culture of two, three or more cell types.

It should also be pointed out that, in the invention, the idea of "porous membrane for cell culture" should be understood as a membrane favouring the adhesion of the cells on the surface thereof and guaranteeing their survival for subsequent culture.

On the other hand, in the invention the idea of "perfusion fluid" refers to a liquid which is slowly and continuously supplied through the inlet duct into at least one of the bioreactor chambers and which exits through the outlet duct.

SUMMARY OF THE INVENTION

It is an object of the invention to provide a bioreactor for cell co-culture of the type indicated at the beginning, which is compact, versatile and which simultaneously allows simple cell co-culture but which, nevertheless, maximizes the viability of the cultured cells and consequently optimizes the time required for carrying out tests.

Furthermore, the bioreactor must be easy to use and must allow the separate analysis of each cell type cultured once the test has terminated.

This object is achieved by a bioreactor and a method for cell co-culture of the type described herein.

As far as the bioreactor of the invention is concerned, unlike the bioreactors known in the state of the art, the membrane already includes its own sealing gasket. A number of synergistically interrelated advantages are derived therefrom.

In the first place, the sealing gasket confers rigidity to the membrane. Thanks to this, the membrane becomes a support which may be handled safely to maintain the cell viability and it is comfortable to seed on this membrane.

Secondly, by the sealing gasket, a cell culture area is defined on which to seed and culture. In other words, the user knows beforehand within which limits of the membrane it is possible to seed to maximize the viability of the culture. This avoids the risk presented by certain bioreactors of the state of the art, in which the assembly of the cultured membrane in the holding frame prior to its assembly in the bioreactor could lead to the crushing or scratching of the cells cultured on the membrane.

Thirdly, the rim formed by the sealing gasket also defines a handling area. Namely, if the membrane is handled with tweezers, the user will know at all times which points of the membrane may be touched, without risk of harming the culture. The sealing gasket itself also defines an easily identifiable holding area.

Fourthly, the sealing gasket does away with an additional member in the bioreactor, since the known bioreactors have a separate gasket that must be sterilized after each use.

Fifthly, the thus configured membrane becomes a low cost disposable consumable item. As a result of this, the cell type seeded on the membrane may be seeded simultaneously on several membranes. Then, the user can choose from among the different seeded membranes the optimum culture for the test within the bioreactor. In this way, the test to be carried out within the bioreactor, at least as far as the cells seeded on the membrane are concerned, has more possibilities of coming to a successful end.

The invention further includes a number of preferred features that are object of the dependent claims and the utility of which will become apparent hereinafter in the detailed description of an embodiment of the invention.

Another of the important objects of the invention consists of facilitating the analysis of the cell type seeded on the membrane. To this end, particularly preferably, said sealing gasket is made of an elastomeric material facilitating its handling and furthermore simplifying its manufacture and allowing costs to be reduced.

With the aim also of improving the versatility of the bioreactor by increasing its possibilities of culturing different cell types, in another embodiment, the bioreactor includes a plurality of separate, mutually parallel membranes assembled in said bioreactor, to form additional culture chambers.

A further object of the invention is to provide a shear stress effect which does not damage the culture on which the stimulus is applied. Thus, preferably, in the bioreactor said first chamber includes at least one perfusion fluid inlet duct discharging into a first flow manifold and at least one outlet duct starting out from a second perfusion fluid flow manifold, said first and second flow manifolds being provided at opposite ends of said first chamber and configured such as to discharge over said membrane distributing said flow across the entire width of said first chamber and in the assembled state of the bioreactor, the space between the first cell culture area of said membrane and at least the bottom of said first chamber is dimensioned to create a laminar flow by said perfusion fluid, said laminar flow having an homogenous velocity over the whole of said first cell culture area.

The flow manifolds serve as a damper for any possible turbulence that the perfusion fluid could cause when entering the first chamber. This damping guarantees the formation of a laminar flow over the entire width of the bioreactor chamber being perfused.

In a preferred embodiment, said first and second flow manifolds are first and second longitudinal grooves deeper than said space between the first cell culture area of said membrane and at least the bottom of said first chamber. The grooves are fully filled before the fluid passes towards the first chamber, whereby the liquid is distributed over the entire width of the first chamber. Thereby, the flow of the perfusion fluid is made uniform in a simple manner before it passes over the central area of the culture chamber. Furthermore, it is achieved that over the entire width of the chamber in which the shear stress effect is applied the flow velocity is substantially homogenous, i.e. that the velocity is the same over the entire width of the chamber. In spite of this, alternatively, the invention contemplates other solutions for distributing the flow over the entire width, such as for example having the horizontal inlet duct branch out progressively in different branches and that these discharge pointwise over the entire width of the first chamber.

It has also been found particularly preferably that to achieve a laminar flow that provides a shear stress effect of protective characteristics, the space between the first face of the membrane and the bottom of first chamber is configured to provide a shear stress effect on said membrane equivalent to the values caused by the blood stream flow in the blood vessels of the human body. As will be seen hereinafter, this feature allows endothelial cells to be stimulated correctly, facilitating the study of the cell paracrine communication.

It has also been found that not all shear stress stimuli enhance the cell growth in the same way. Particularly, it has been found that when the perfusion fluid flow according to the invention reproduces the tangential flow conditions existing in the real flow vessels, the results improve. Thus, preferably, the shear stress effect is between 0.1 and 20 $N/m^2$, and preferably between 0.3 and 3 $N/m^2$, which come closest to the values of the blood vessels of the human body. Thanks to this, the maintenance of a correct culture is favoured.

In a preferred embodiment, said membrane includes a second sealing gasket integrated in said membrane being integral therewith and said second sealing gasket defines a closed perimeter enclosing a second cell culture area. This allows seeding on both sides of the membrane.

In spite of it not being essential for the invention, it may be desirable to achieve a repeatability of the assembly of the membrane in the bioreactor. To this end, in one embodiment there is provided a perimetrical groove adjacent to at least said first chamber and said first sealing gasket is configured to fit in said perimetrical groove and to provide fluid-tight conditions in the assembled state of said bioreactor.

During a test in the bioreactor, it may be necessary to verify the state of the cell culture. This may require disassembling the bioreactor, which may have a prejudicial effect on the test. Therefore, to facilitate the verification and control of the cells in the bioreactor, in an alternative embodiment the bioreactor includes a housing of transparent material in at least part of the area corresponding to said first and second chambers.

Also, depending on the dimensions of the bioreactor, it may be necessary to protect the membrane against rupture by bending. Thus, in a preferred embodiment, the bioreactor includes a support arranged under said membrane such as that in the position of use of said bioreactor said membrane rests, at least in part, on said support so as to preclude or reduce the bending of the membrane due to the weight of the culture and/or of the perfusion fluid. Consequently, the risk of rupture of the membrane while the test is being carried out is eliminated and, on the other hand, by reducing the bending, a more constant height of the chamber formed by the membrane is achieved. Thus, a more homogenous shear stress stimulus is achieved.

In a preferred embodiment, said support is at least one support column, said at least one support column being provided in the center of said second chamber and having a height such that, in the assembled state of said bioreactor, said membrane may rest on said at least one support column. In an alternative embodiment, said support is a grid provided under the membrane.

On the other hand, it may be necessary to carry out parallel tests to compare results under variable conditions. For example, one test simulates neutral reference conditions, while the parallel test studies the effects of the application of a drug to the culture. To this end, the bioreactor 13 has at least two inlet ducts and at least two outlet ducts and said first or second sealing gaskets include at least one longitudinal partition wall delimiting independent closed cell culture areas on said membrane and which in the assembled state of said bioreactor are fluid-tight and said at least one longitudinal partition wall is orientated in such a way as to separate one pair of inlet and outlet ducts from another adjacent pair of inlet and outlet ducts.

Particularly preferably, when the bioreactor has a partition of the membrane into two sub-chambers, said support column extends along said second chamber, dividing it into two and being arranged such as to coincide with the position of said longitudinal partition wall in such a way that in the assembled state of said bioreactor said longitudinal partition wall rests on said support column.

Finally, in a preferred embodiment, the bioreactor has an air purge chimney in said at least one inlet duct to evacuate any bubble existing in the perfusion circuit. Particularly preferably, this chimney is provided at a point along the perfusion fluid inlet duct. This chimney allows any air bubbles which may form at the time of closing the bioreactor to be evacuated.

Likewise, the invention also includes other features of detail illustrated in the detailed description of an embodiment of the invention and in the accompanying figures.

BRIEF DESCRIPTION OF THE DRAWINGS

Further advantages and features of the invention will become apparent from the following description, in which, without any limiting character, preferred embodiments of the invention are disclosed, with reference to the accompanying drawings in which:

FIG. 1 is an exploded perspective view of the bioreactor of the invention with the cover oriented towards the viewer.

FIG. 2 is a cross section view of the bioreactor membrane along the line II-II of FIG. 1.

DETAILED DESCRIPTION OF EMBODIMENTS OF THE INVENTION

Figure 3:
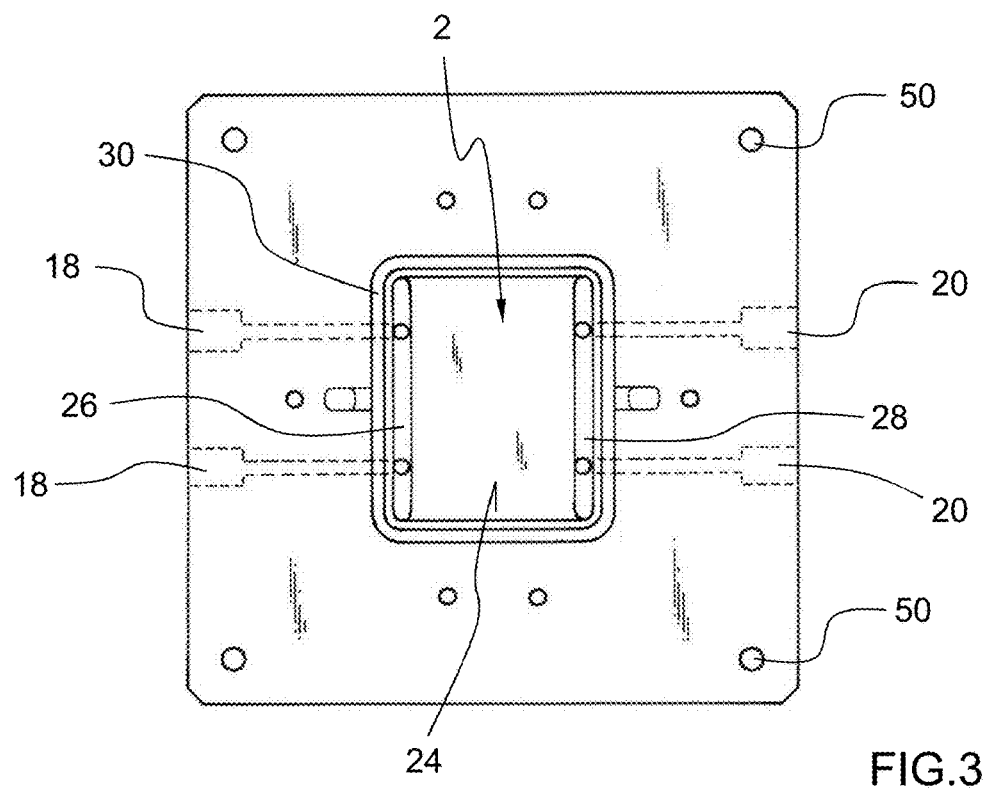
FIG. 3 is a plan view of the inner face of the cover of the bioreactor of FIG. 1.
Figure 4:
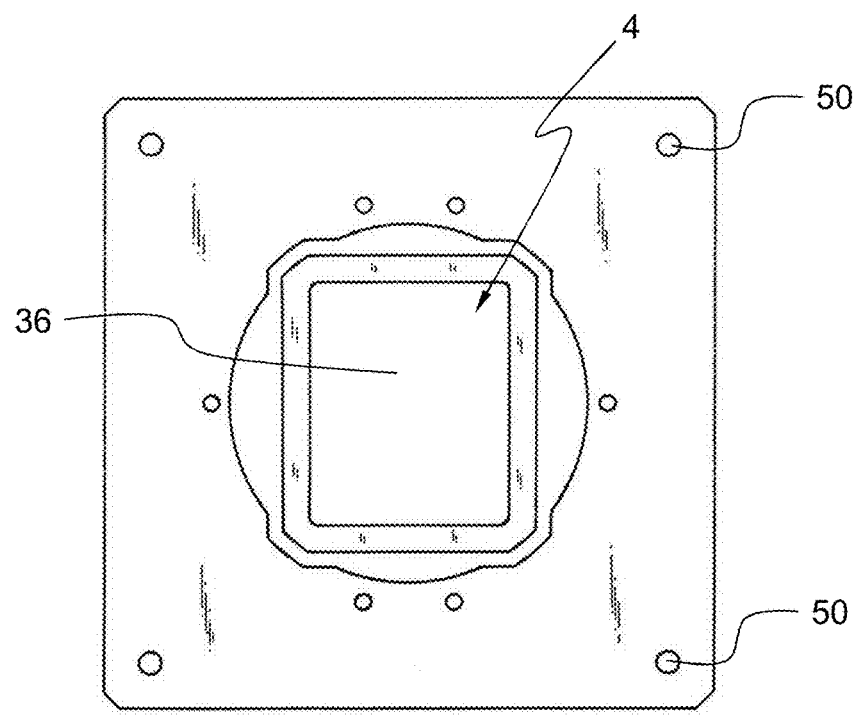
FIG. 4 is a plan view of the inner face of the base of the bioreactor of FIG. 1.
Figure 5:
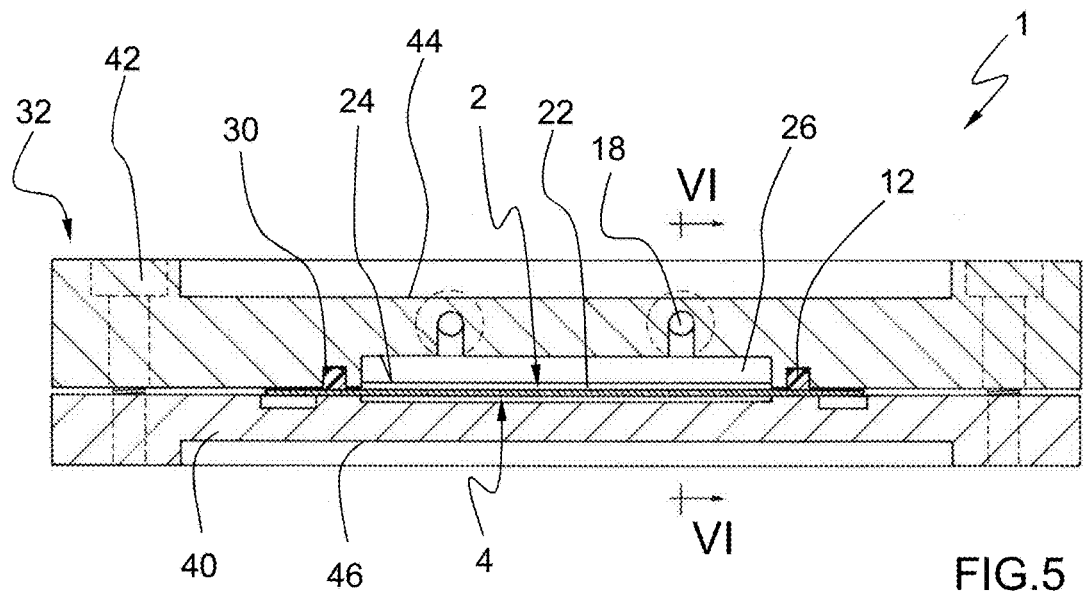
FIG. 5 is a longitudinal section view along the line V-V of FIG. 6 of the bioreactor of FIG. 1.

FIGS. 1 to 7 show a first embodiment of the cell co-culture bioreactor 1 of the invention.

The bioreactor 1 includes an 80×80 mm quadrangular housing 32 formed by a base 40 and a cover 42 which can be disassembled from one another. The housing 32 is made of materials which do not interfere in the cell culture. The materials suitable for this type of applications are, for example, aluminium, stainless steel or thermoplastics such as polymethylmethacrylate (PMMA), polystyrene, polycarbonate and polytetrafluoroethylene or glass, or combinations thereof. Nevertheless, it is preferable for the cultures to be able to be observed under a microscope without the need for disassembling the bioreactor 1. Therefore, particularly preferably, the housing 32 is made of transparent polymethylmethacrylate. This allows it to be manufactured simply, for example by machining or by injection moulding.

The membrane 6 is a porous sheet suitable for cell culture including a closed sealing gasket 12, integrated in the membrane 6, being integral therewith. Furthermore, for its configuration, the membrane 6 is a disposable consumable item, whereas on the contrary the housing 32 may be reused a plurality of times after the corresponding sterilization process. The sealing gasket 12 defines a closed perimeter delimiting a first cell culture area 16.

Inner recesses forming first and second cell culture chambers 2, 4 are provided on the inner surfaces of the base 40 and cover 42. The chambers are separated from one another by the membrane 6. The bioreactor 1 may be disassembled by separating the cover 42 and base 40 to have access to both culture chambers.

In the cover 42, the first chamber 2 has a first flow manifold configured as a first longitudinal damper groove 26, into which there discharges at least one perfusion fluid inlet duct 18. At the opposite end of the first chamber 2 there is provided a second flow manifold which is also configured as a second longitudinal damper groove 28 from which there starts out a perfusion fluid outlet duct 20. Alternatively, both the first and second flow manifolds could be configured in a different way, such as for example as a duct branching out across the entire width of the bioreactor 1. In this second case, the solution may be implemented as a horizontal inlet duct 18 machined on the inner surface of the cover 42. This inlet duct 18 branches out into a plurality of auxiliary ducts which finally end in a small groove provided on the end wall of the first chamber 2.

Figure 6:
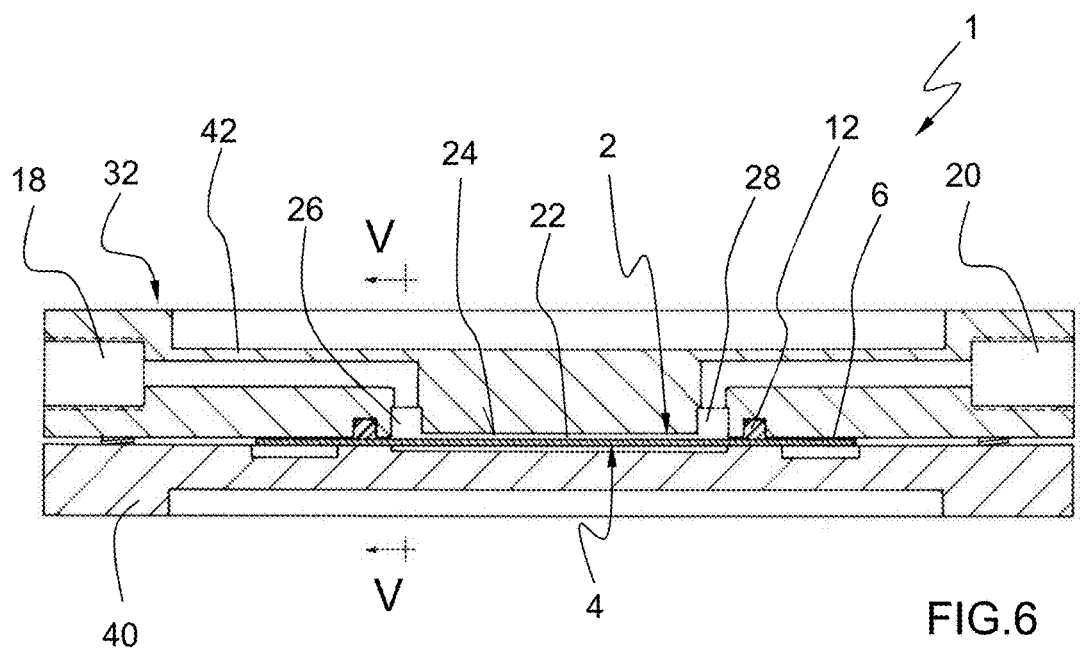
FIG. 6 is a longitudinal section view along the line VI-VI of FIG. 5 of the bioreactor of FIG. 1.

Turning back to the bioreactor of the figures, as is to be observed particularly in FIG. 6, the opening formed by the first and second grooves 26, 28 is orientated towards the first culture area 16, namely, that on entering the bioreactor 1, the perfusion fluid falls on the membrane 6 in the area corresponding to the first groove 26. In this embodiment, the grooves measure 2.6 mm wide by 1.6 mm deep, extending along the entire width of the first chamber 2 to guarantee a good distribution of the perfusion fluid.

In this same FIG. 6, it is also to be observed that the bottom 24 of the first culture chamber 2 is very close to the first surface 8 of the membrane 6. Particularly, the space 22 between the membrane 6 and the bottom 24 of the first chamber 2 is dimensioned top create a laminar flow of homogenous velocity across the entire width of the first cell culture area 16 by the perfusion fluid. For example, in the bioreactor 1 of FIGS. 1 to 7, being 80×80 mm in plan and about 15.5 mm high, and with a width of the first chamber 2 of 32 mm, the space 22 is 500 µm (micrometers).

The combination of this space 22 with the grooves 26, 28 provides a laminar flow crossing the first chamber 2 and providing a shear stress effect having protective characteristics. It has been found that the shear stress effect on the membrane 6 reproducing these protective characteristics is the equivalent to the values caused by the blood stream flow in the blood vessels of the human body. In more detail, it has been proven that the preferred values of the shear stress effect of protective characteristics are in the range of 0.1 to 20 N/m$^2$ and particularly preferably of 0.3 to 3 N/m$^2$.

Coming back to the functional features of the bioreactor of the invention, the perfusion fluid discharges through the inlet duct 18 into the first groove 20. In spite of this, it does not significantly enter in the space 22 until it has flooded the first groove 26, which makes the flow uniform along the entire first groove 26. Once this situation has been reached, the fluid enters the space 22 guided between the surface of the membrane 6 and the bottom 24 of the first chamber 2, which guarantees the formation of a laminar flow of constant velocity across the entire width of the bioreactor 1.

Furthermore, there is provided in the cover 42 a perimetrical groove 30 adjacent the first chamber 2 and provided for the sealing gasket 12 to fit therein, so as to provide fluid-tight conditions when the bioreactor 1 is in the assembled state.

Finally, an upper recess 44 is provided on the upper surface of the cover 42 which enhances even more the visibility of the cells cultured in the first chamber 1.

The base 40 is also provided with a second chamber 4 with a central recess defining a cell culture area 36. Additionally, around the central recess there is provided an external reservoir 48 allowing excess fluid when culturing to be stored. Likewise, at the lower part thereof, the base 40 also has a lower recess 46 improving the observation of the second culture chamber 4.

The fluid-tightness of the bioreactor 1 is achieved by tightening the base and cover 40 with screws housed in holes 50 provided in both parts. On tightening the base 40 and the cover 42 together, with the membrane 6 assembled between them, the sealing gasket 12 is compressed and it is thus achieved that the system is fluid-tight during the perfusion.

As has already been mentioned above, the membrane 6 of the invention is porous and must be suitable for cell culturing, namely, it must have the necessary features for facilitating the adhesion and growth of cells on its surface. In its most general form, the porous membrane 6 is a hydrophilic polytetrafluoroethylene membrane, more commonly known as PTFE, available on the market, having an outer diameter of 47 mm and 1 µm (micrometer) pores. One example of this type of membrane is the Omnipore® membrane marketed by the Merck Millipore Corporation. In alternative embodiments, the membrane 6 could be replaced by a membrane made of any other material depending on the required application, for example a natural or biodegradable synthetic polymer, such as polyester, polylactic acid, polyvinyl alcohol, polyolefins, alternatively a plastic such as polycarbonate, cellulose, etc.

In a preferred embodiment, the sealing gasket 12 has been made of a silicone elastomeric adhesive, such as for example, Loctite® 5055 Silicone of Henkel®. This adhesive, when duly cured, defines the cell culture area 16 and, moreover, assumes the function of a ring seal, so that the chamber is fluid-tight under perfusion. Preferably, the membrane 6 is between 5 and 200 µm (micrometers) thick.

In a preferred manufacturing process of the membrane 6, the following steps are considered: a mould, for example of methacrylate, is manufactured by milling, with the negative of the sealing gasket 12 to be manufactured. Because of its simplicity, the mould is not shown in the figures. Then, the mould is filled with the silicone and is covered with the membrane 6 so that the silicone can diffuse therethrough. Thereafter, the silicone is exposed to ultraviolet light to cure the silicone, achieving the immobility of the sealing gasket 12 on the sheet 34. Finally, the membrane 6 is removed from the mould. A sealing gasket suitable for the bioreactor 1 has an approximately semi-circular cross section of 2.3 mm diameter.

Thanks to the sealing gasket 12, the membrane 6 of the invention can be used as a culture support independent from the bioreactor 1. Thus, once the cells have been cultured, the membrane 6 is handled normally with tweezers. To this end, the sealing gasket 12 is provided with two projections 34 which provide an additional handling area of the membrane 6 specially removed from the culture area 16 to minimize the risk of harming the culture with the tweezers.

In this embodiment, two inlet ducts 18 and two outlet ducts 20 have been shown in the cover 42. One of these pairs (inlet/outlet) of ducts 18, 20 can be sealed, cancelling out their use.

Figure 14:
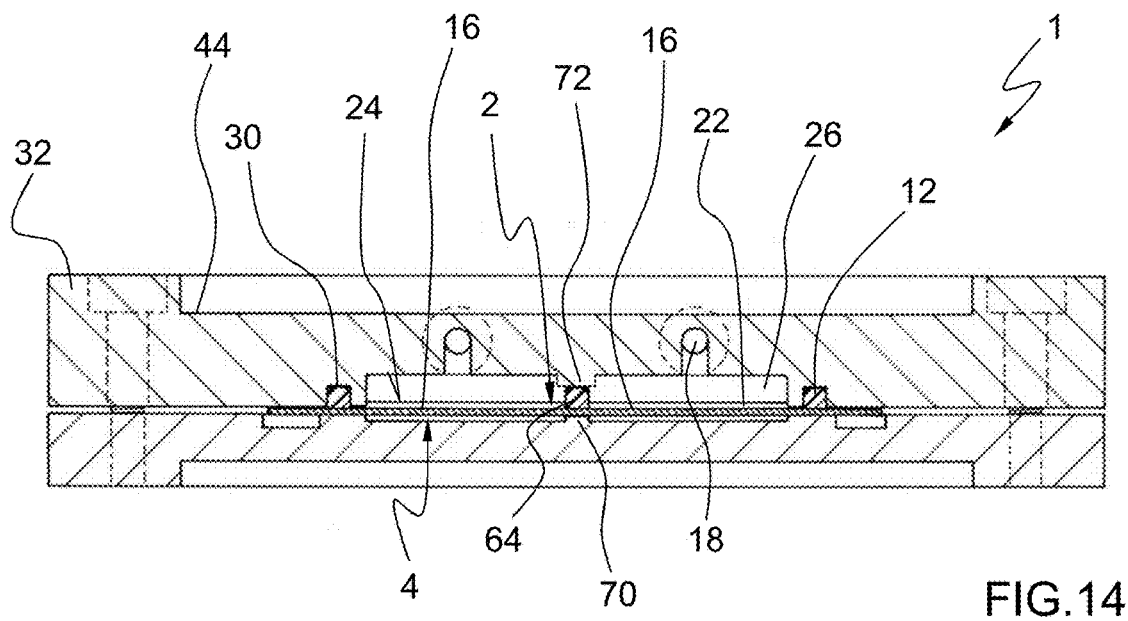
FIG. 14 is a longitudinal section view of an eighth embodiment of the bioreactor of the invention.

Nevertheless, in an alternative embodiment, shown in FIG. 14, the bioreactor 1 includes two or more inlet ducts 18 and a like number of outlet ducts 20. Then, the first or second sealing gaskets 12, 14 include at least one longitudinal partition wall 64 delimiting independent closed cell culture areas on the membrane 6. The longitudinal partition wall 64 is also made of the same elastomeric material as the sealing gaskets 12, 14, so as to be integral therewith. Furthermore, the longitudinal partition wall 64 is orientated in such a way as to separate a pair of inlet and outlet ducts 18, 20 from another adjacent pair of inlet and outlet ducts 18, 20.

Furthermore, the second chamber 4 has support configured as a support column 70 in the centre of the second chamber 4. This column projects from the bottom of the second chamber 4 as a transverse rib dividing the second chamber into two halves. The support column 70 is arranged relative to the cover 42 and the membrane 6 so as to coincide with the position of the longitudinal partition wall 64.

In the assembled state of the bioreactor 1, the longitudinal partition wall 64 of the membrane 6 is compressed between a projection 72 projecting from the cover 42 and the support column 70 of the base 40. In this way, each of the cell culture areas separated by the longitudinal partition wall 64 is fluid-tight. Alternatively, the support column 70 could be replaced by a second longitudinal partition wall in the sealing gasket 14 that would be compressed against the base 40.

Each of these cell culture areas 16 is associated with its respective pair of inlet and outlet ducts 18, 20. This allows different tests to be performed in one same bioreactor 1. For example, in one of the areas a test is performed with a simple perfusion fluid, while a drug is tested on the other area. In this way, a comparative test is available on the effect of the drug on the cells cultured in the second lower chamber, with the cells coming from one same seeding and having identical environmental conditions, except for the drug itself.

In spite of the existence of the inlet and outlet ducts 18, 20, the bioreactor 1 of the invention can be used both in static tests and in dynamic tests, namely, by applying a shear stress effect by a perfusion system.

Figure 7:
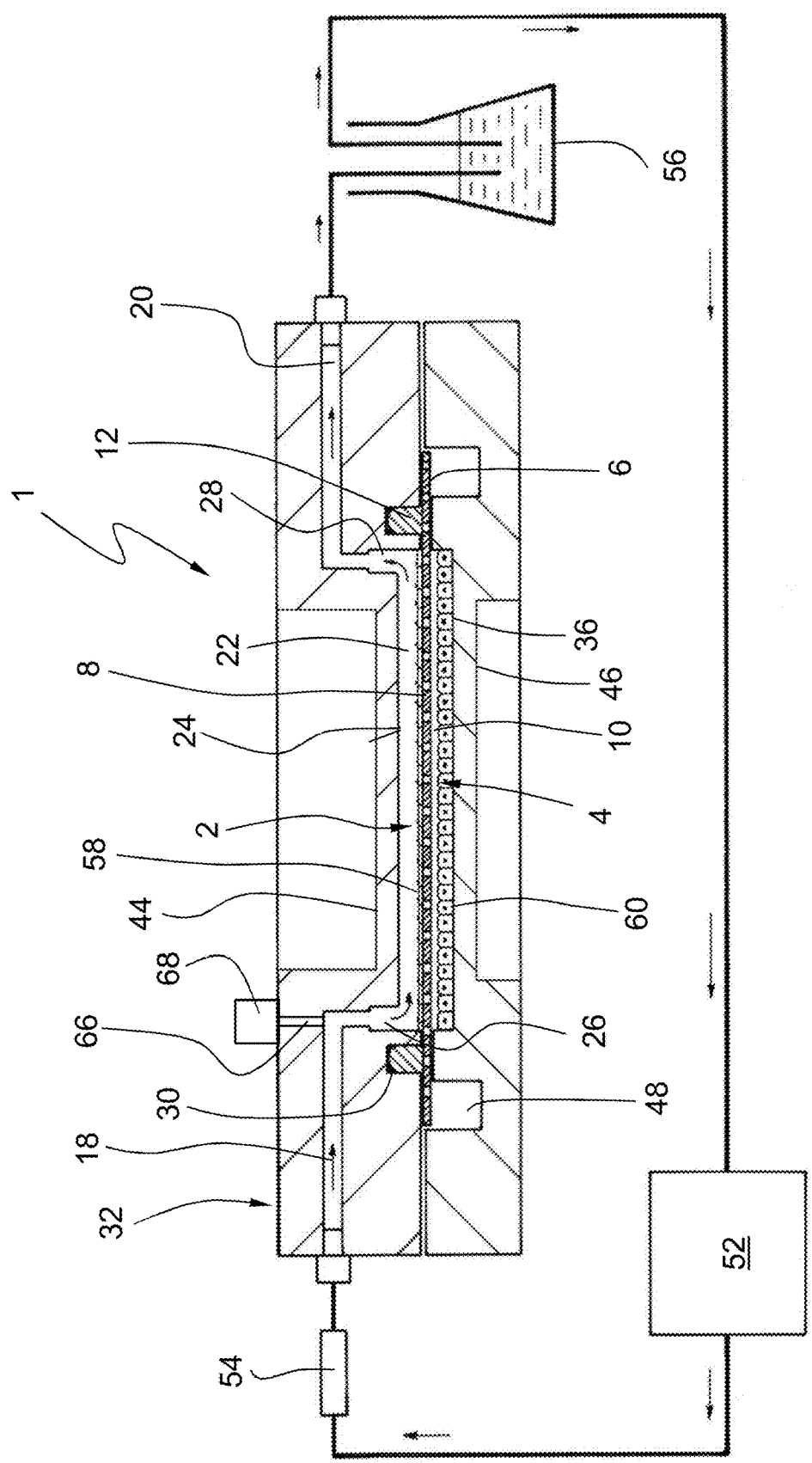
FIG. 7 is an assembly diagram of a perfusion system using the bioreactor of the invention.

FIG. 7 shows the application of the bioreactor 1 in the case of a cell co-culture with shear stress. The perfusion system consists of a peristaltic pump 52 which draws the perfusion fluid from a container 56. The perfusion fluid is injected in the first culture chamber 2 through the inlet duct 18 and first groove 26. The outlet from the first culture chamber 2 is connected directly to the container 56 through the second groove 28 and the outlet duct 20, such that the system is recirculating.

Before the inlet to the first culture chamber 2 there is installed a bubble trapping device 54, for example the Speedflow model, marketed by the GVS company which prevents the bubbles that may be generated in the system from reaching the first culture area 16, distorting the shear stress effect. The bioreactor 1 also preferably includes an air purge system in the inlet duct 18, which in this case consists of a chimney 66. This chimney 66 has been shown only schematically in FIG. 7, sealed by a plug 68. It is not uncommon that during assembly an air bubble is trapped inside the bioreactor 1 on closing it and that the bubble trap device 54 is not capable of removing it. Thanks to the purge chimney 66, this bubble is easily removable.

The embodiments of bioreactors 1 described hereinafter share a large number of the features of the first embodiment. Consequently, with regard to the description of said common features, the description of FIGS. 1 to 7 is incorporated by reference.

Figure 8:
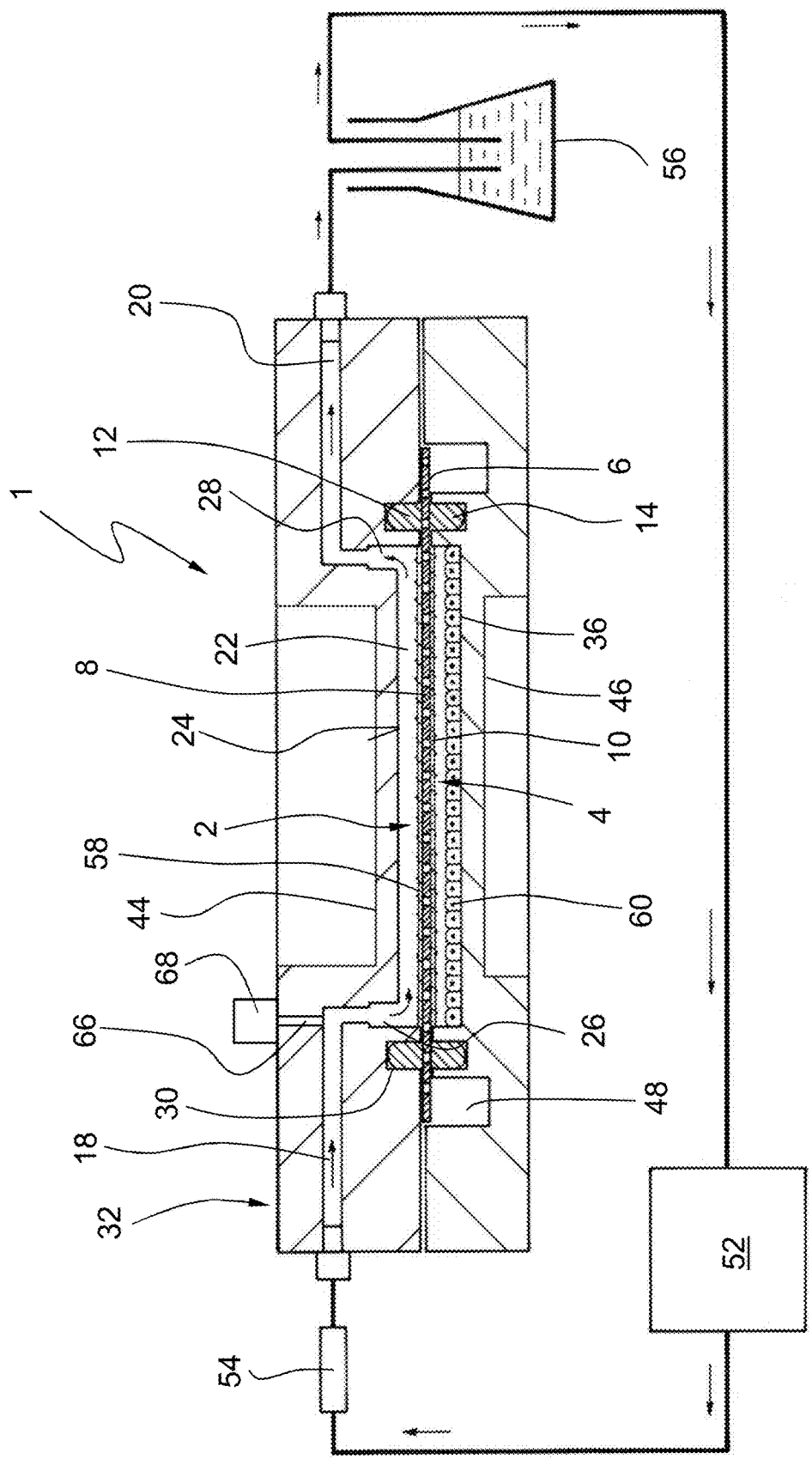
FIG. 8 is an assembly diagram of a perfusion system using a second embodiment of the bioreactor of the invention.

The bioreactor of FIG. 8 has a membrane 6 having on the second surface 10 thereof a second sealing gasket 14 incorporated in the same way as the first sealing gasket. Thereby, this membrane 6 may be cultured on both sides, taking advantage of the beneficial effects explained with regard to the first sealing gasket 12. Also as shown in this figure, the shear stress stimulus in this bioreactor 1 is only applicable in the first chamber 2.

Figure 9:
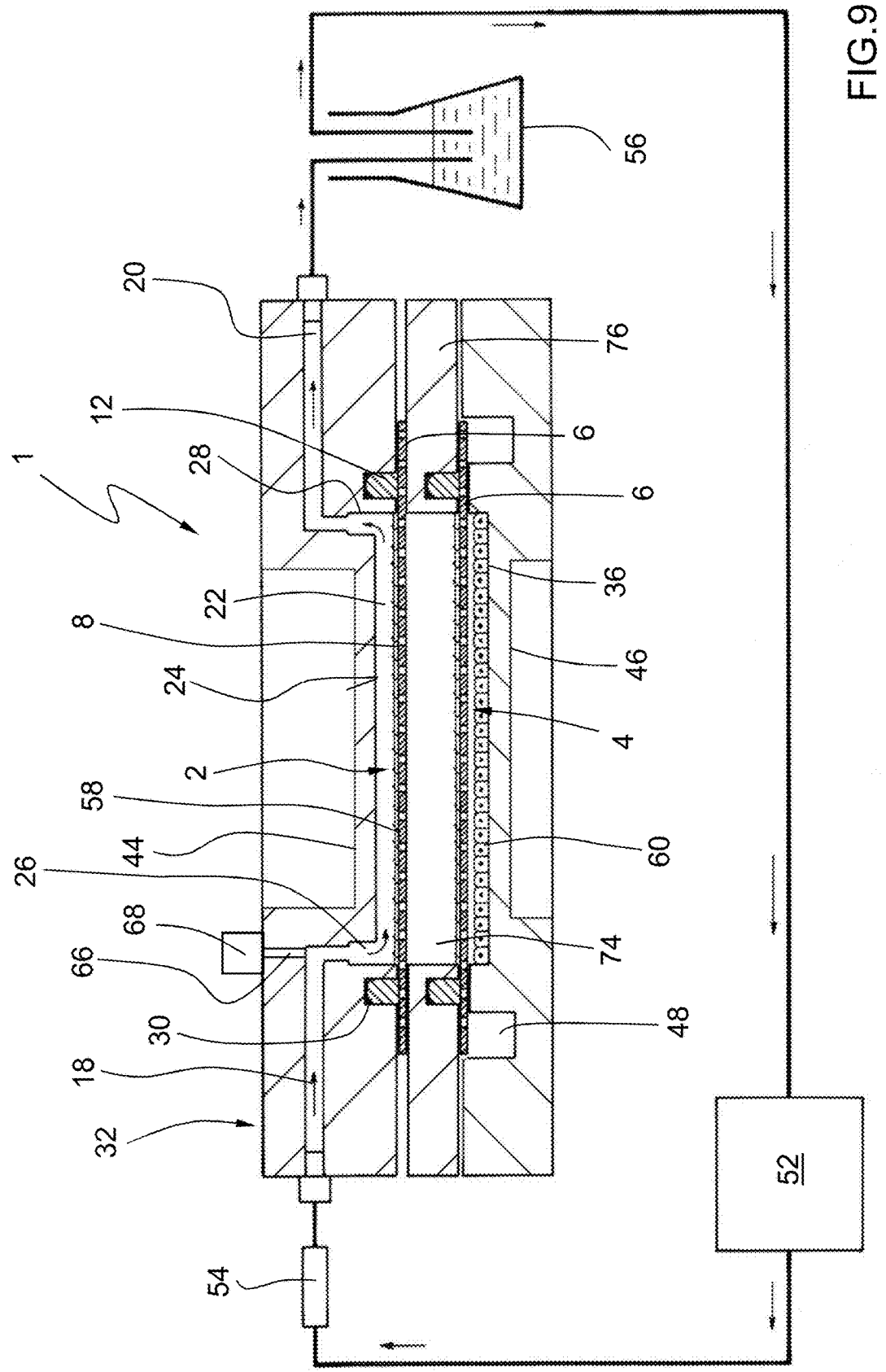
FIG. 9 is an assembly diagram of a perfusion system using a third embodiment of the bioreactor of the invention.

FIG. 9 shows a third embodiment of a bioreactor 1 of the invention with a plurality of membranes 6. As is to be seen in the figure, in this case, the bioreactor 1 has two separate, mutually parallel membranes 6 of identical characteristics, forming an intermediate culture chamber 74. To guarantee the correct positioning of both membranes 6, there is provided a frame 76 including a perimetrical groove in which the first sealing gasket 12 of the second membrane 6 is inserted. The frame 76 is assembled as a sandwich structure between the cover 42 and the base 40, the features of which have already been described above. Three differentiated types of cell can easily be cultured in this bioreactor 1. It should also be said that in this embodiment the shear stress stimulus can only be applied in the first chamber 2. Nevertheless and in spite of not being shown, it could be contemplated that the frame 76 were also to incorporate corresponding ducts for applying the shear stress stimulus in the intermediate chamber 74. Also, the invention does not exclude the possibility of combining several intermediate parts which would allow the construction of a bioreactor 1 provided with multiple membranes 6, with or without the possibility of applying a shear stress stimulus.

Figure 10:
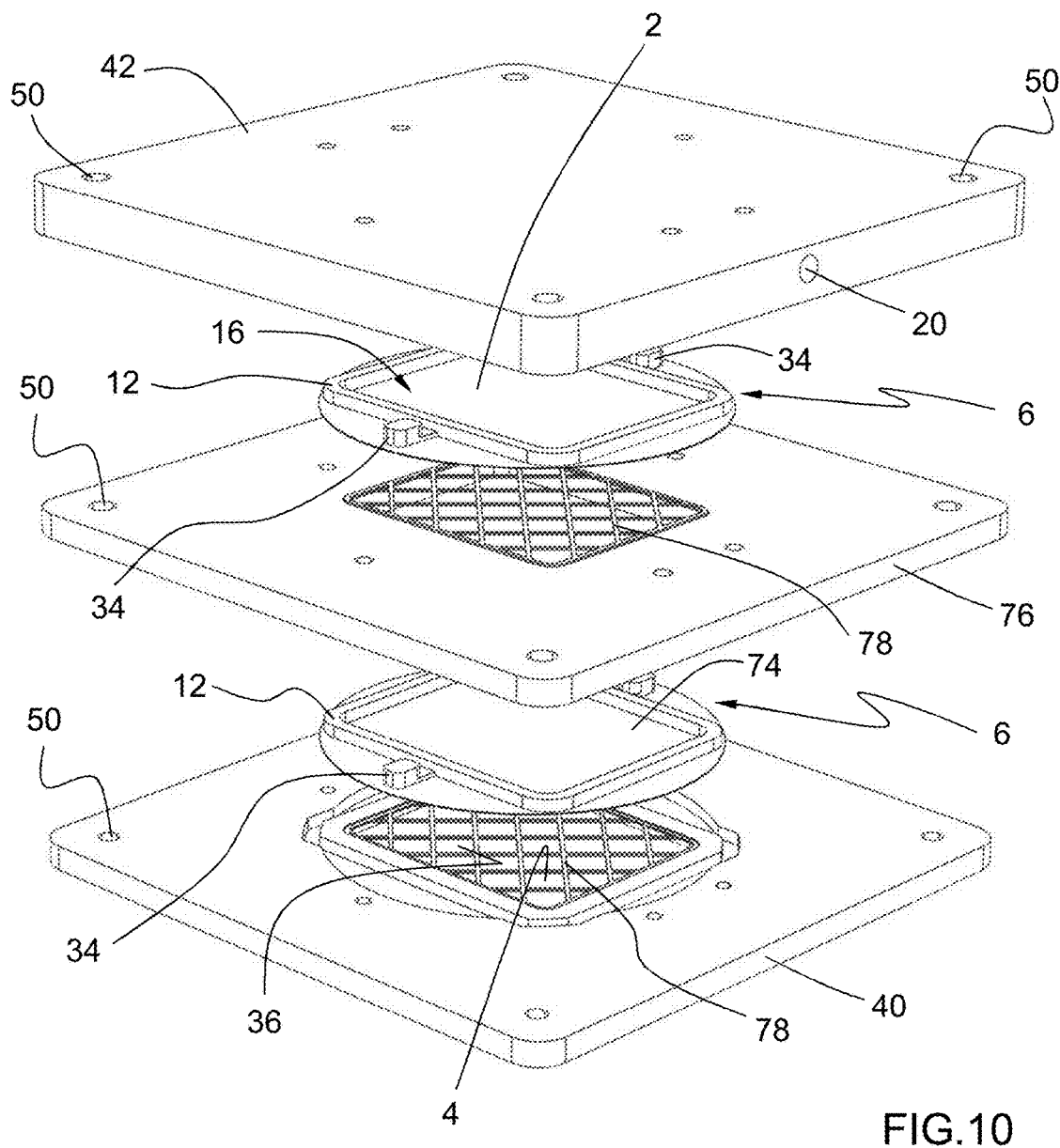
FIG. 10 is an exploded perspective view of a fourth embodiment of the bioreactor of the invention.

The fourth embodiment of FIG. 10 is also a sandwich type structure of bioreactor 1 with two membranes 6 defining a first chamber 2, an intermediate chamber 74 and a second chamber 4. The main difference of this embodiment lies in the fact that the bioreactor 1 includes a grid-like 78 support arranged under said membrane 6 such that in the position of use of the bioreactor 1, the membrane 6 is supported, at least in part, on said support. The same as in the case of the column of the FIG. 14 embodiment, the grid prevents the bending of the membrane 6. The grid 78 corresponding to the lower membrane 6 rests on the second chamber 4, while in the case of the upper membrane 6, it rests on the frame 76.

This grid 78 prevents undesired stresses in the membranes 6 caused by excessive bending. On the one hand, this avoids the risk of undesired ruptures and on the other hand, it makes the shear stress stimulus more homogenous, since it is easier for the space 22 to remain constant over the entire extension of the corresponding culture chamber. The grid may have any desired structure, with the sole condition of being completely permeable to the perfusion fluid. Likewise, the grid 78 could be applied to any embodiment of the bioreactor 1, since it is not essential for the bioreactor 1 to have more than one membrane 6.

Figure 11:
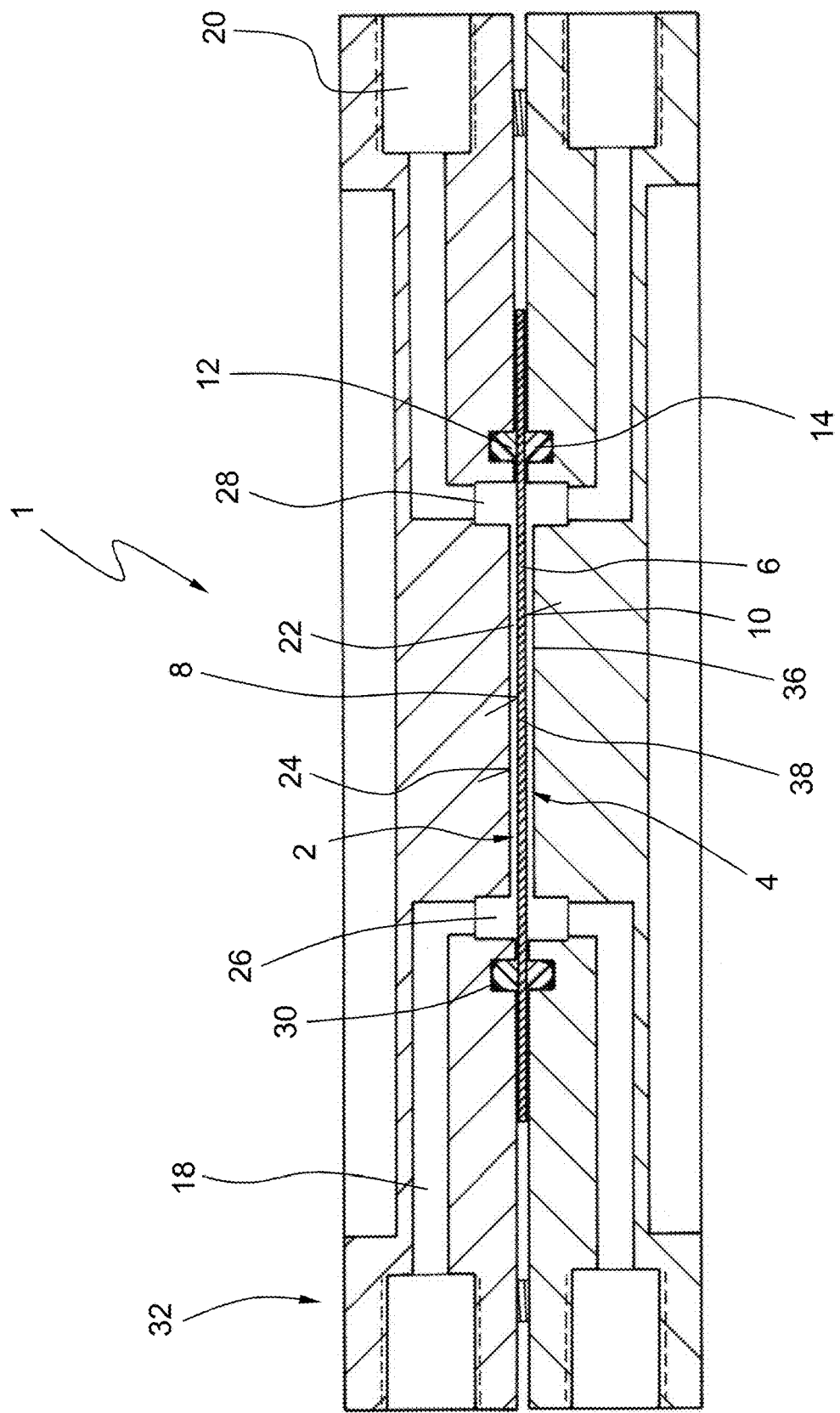
FIG. 11 is a longitudinal section view along a median plane of a fifth embodiment of the bioreactor of the invention.

FIG. 11 shows a fifth embodiment of the bioreactor 1 of the invention. The substantial difference in this embodiment consists of the base 40 of the first embodiment having been replaced by a part identical to the upper cover 42. This allows for the application of perfusion fluid flow on both sides of the membrane 6. Likewise, the membrane 6 includes a second sealing gasket 14 integrated on the second surface 10 defining a closed perimeter enclosing a second cell culture area 38 on the membrane 6. The same as in the previous case, the first and second sealing gaskets 12, 14 are integral with the membrane 6, such that they provide the advantages disclosed in the summary of the invention. Thus, this embodiment allows the culturing of a second cell type on the second side 10 of the membrane 6, thereby facilitating the interaction of three cell types.

Figure 12:
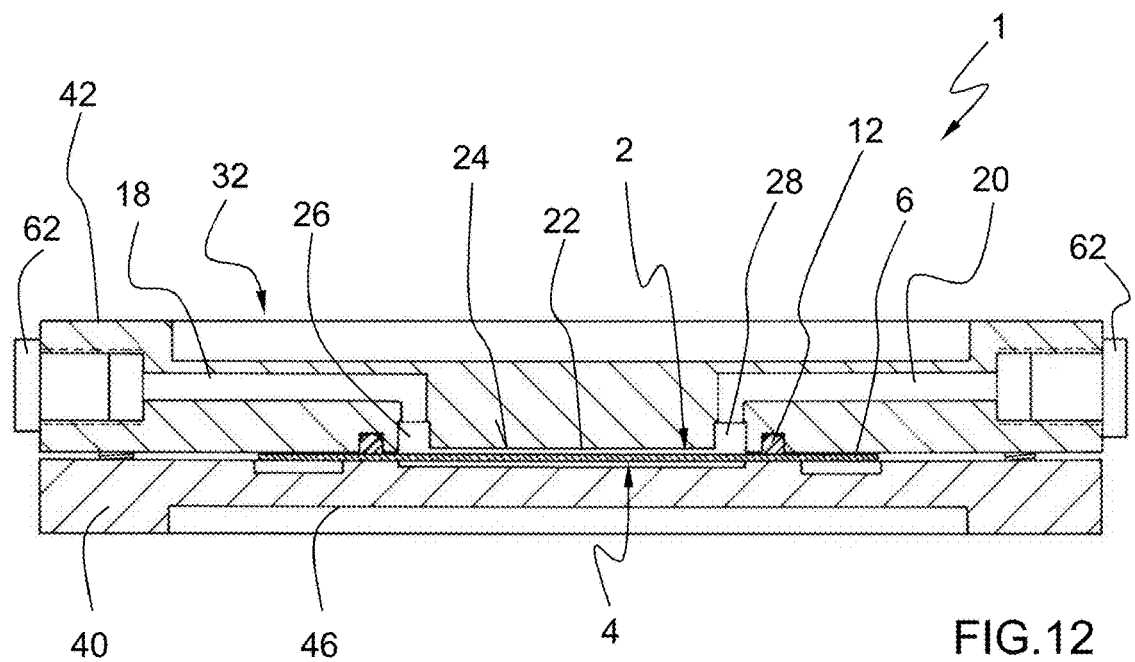
FIG. 12 is a longitudinal section view along a plane of a sixth embodiment of the bioreactor of the invention.

FIG. 12 shows a sixth embodiment of the bioreactor 1 of the invention. This bioreactor 1 is devised for carrying out tests under static and/or dynamic conditions. To be able to carry out the test statically, the bioreactor 1 is provided with stoppers 62 of the inlet and outlet ducts 18, 20.

Figure 13:
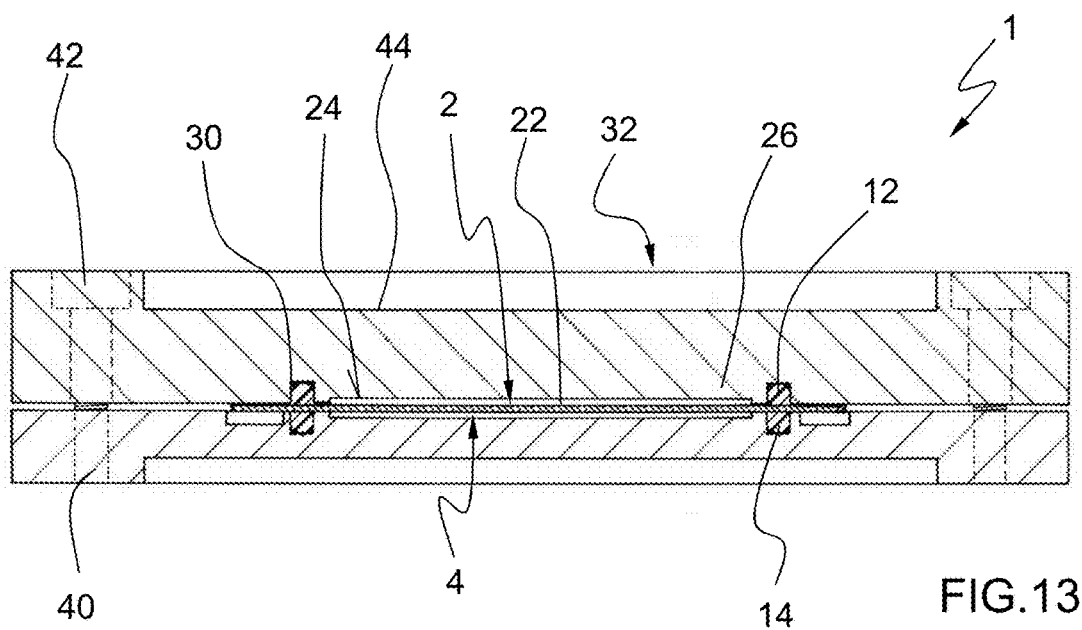
FIG. 13 is a longitudinal section view of a seventh embodiment of the bioreactor of the invention.

Alternatively, in a simplified version of the bioreactor 1 of FIG. 12, the bioreactor 1 shown in FIG. 13 does not have inlet and outlet ducts 18, 20 either in the cover 42 or in the base 40. In this way, this bioreactor 1 only allows tests to be carried out under static conditions.

Example 1

In this test a preferred embodiment of the bioreactor 1 of the invention provided with perfusion fluid inlet and outlet ducts 18, 20, like the one shown in FIG. 7 was used.

Primary human umbilical vein endothelial cells 58 (HUVEC) were cultured on the membrane 6, previously treated with gelatin. Endothelial cells 58 have been widely validated as "gold standard" for vascular biological studies. Hepatic stellate cells 60 were cultured in the second chamber 4. After the seeding of both cell types independently, the bioreactor 1 was assembled. A shear stress stimulus of 0.3 N/m² was applied in the first chamber 2 for 24 h through the first inlet duct 18. The stimulus only directly affected the endothelial cells 58 seeded on membrane 6.

Figure 16:
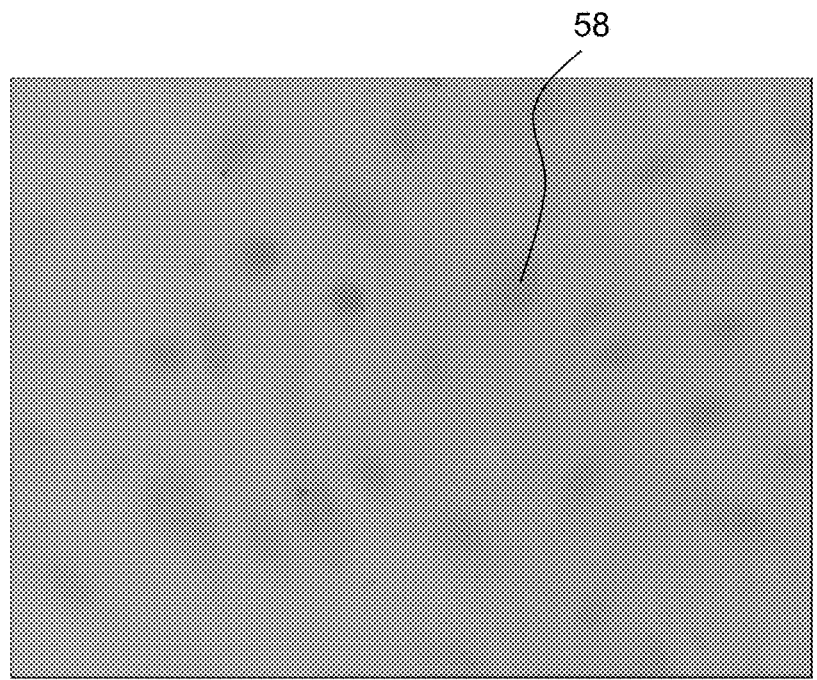
FIG. 16 is an image of the staining of endothelial cells with DAF-FM under static conditions to observe the production of nitric oxide in real time.
Figure 17:
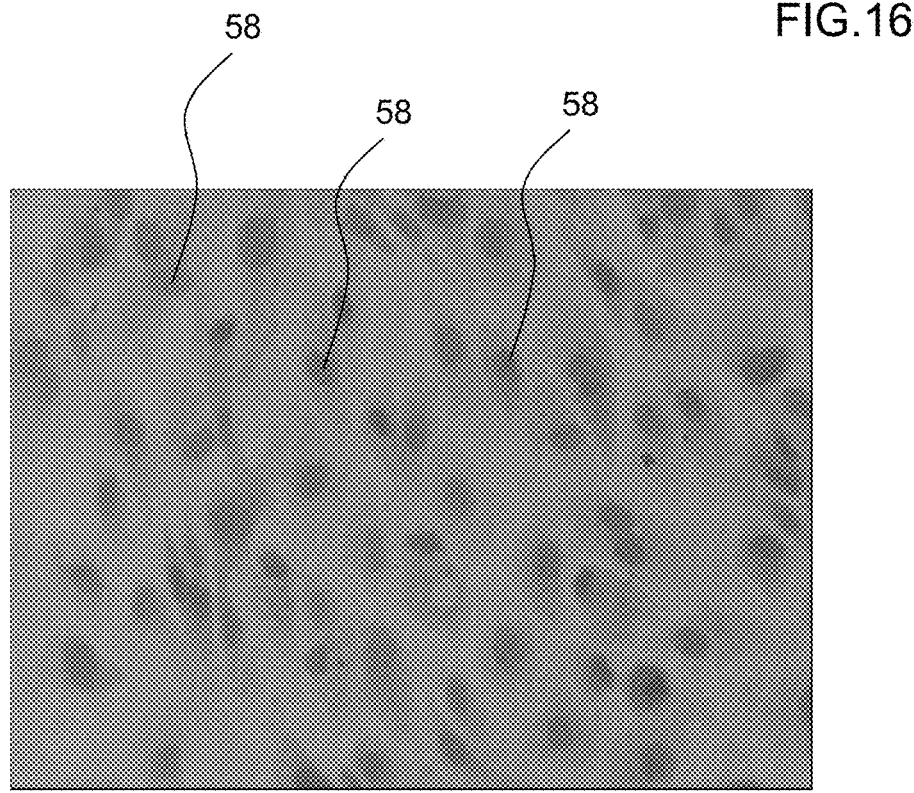
FIG. 17 is an image of the staining of endothelial cells with DAF-FM under continuous shear stress perfusion to observe the production of nitric oxide in real time.

After the 24 hours has elapsed, the bioreactor 1 was disassembled, the two cell types were separated and the morphology of the endothelial cells 58 was analyzed by staining the membranes and nuclei with Image-IT® LIVE Plasma Membrane and Nuclear Labeling Kit, marketed by Invitrogen. In the endothelial cells 58 the production in real time of nitric oxide was also analyzed by staining with DAF-FM diacetate (4-Amino-5-Methylamino-2',7', Difluorofluorescein Diacetate), also marketed by Invitrogen. The result of said analysis is clearly to be seen in FIGS. 15 to 17. The staining of membranes and nuclei allowed the morphological state, the adherence and the alignment of the cells after the shear stress stimulus to be known. FIG. 16 shows the result in the case of static culturing, whereas FIG. 17 shows the case with the application of the shear stress stimulus. It should be said that to enhance the observation of the fluorescent staining of the endothelial cells 58, FIGS. 16 and 17 show the negative of the image observed after staining, namely, the fluorescent labeling would be appreciated in lighter tones, whereas the rest of the image would be darker.

Figure 15:
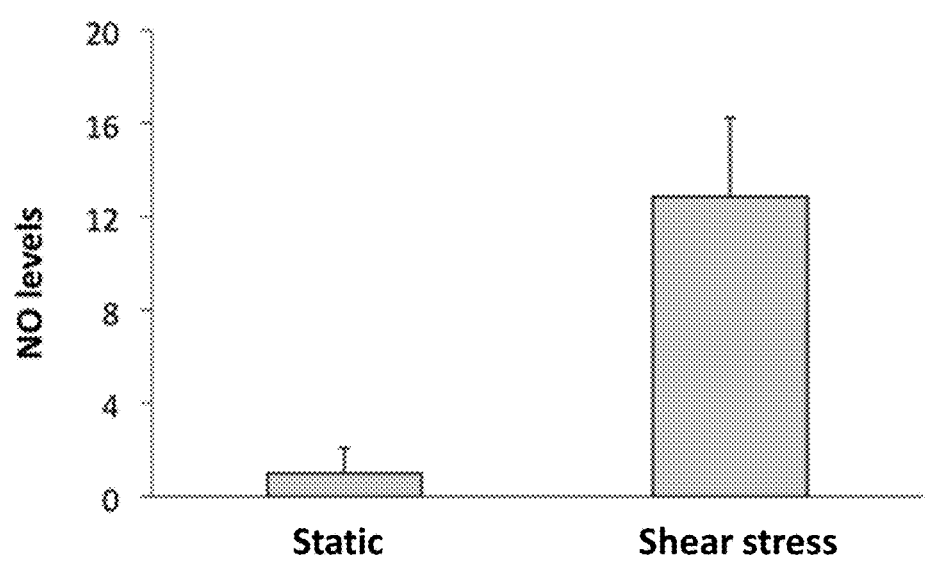
FIG. 15 is a comparative diagram of the production of nitric oxide under static conditions and under shear stress.
Figure 18:
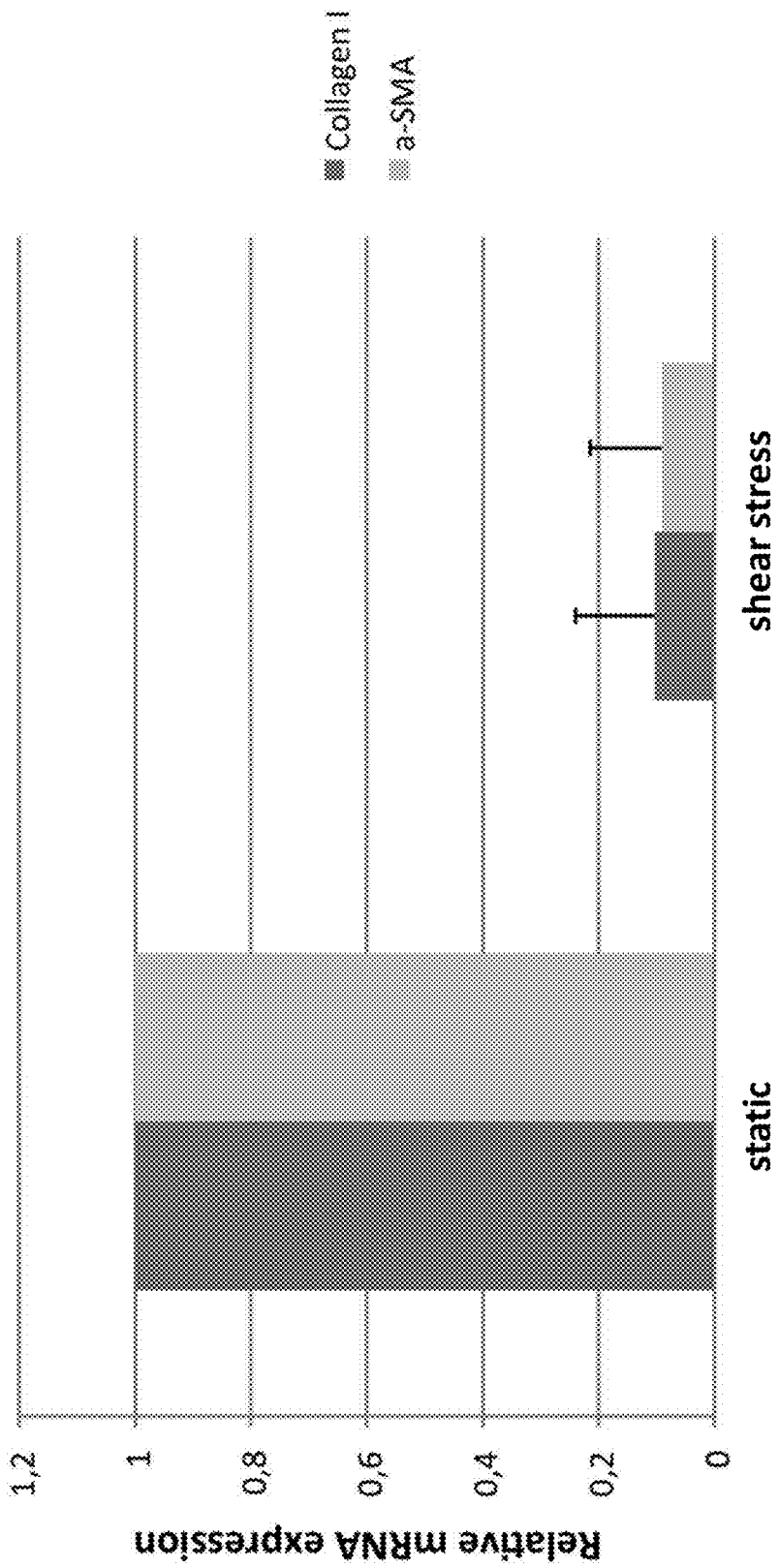
FIG. 18 is the analysis of the expression of mRNA of two activation markers in hepatic stellate cells.

As the skilled person knows, the nitric oxide production is a functional test to check the induction of a correct endothelial phenotype derived from the biomechanical shear stress stimulus, as is to be seen in FIG. 15. Furthermore, the hepatic stellate cells 60 were processed to analyze the genic expression of their main "activated" state markers (characteristic of cells having a proinflammatory, proliferative and vasoconstrictive phenotype), the smooth muscle actin (a-SMA) and collagen I (col. I) by polymerase chain reaction (PCR) in real time. FIG. 18 shows that there is a clear reduction in the activated state, collagen I and a-SMA markers, indicating an improvement in the phenotype of the hepatic stellate cells 60, derived from the production of nitric oxide by the endothelial cells 58 under shear stress conditions.

The test included the control condition consisting of carrying out the process with cells cultured in the bioreactor 1, but under static conditions, i.e. without shear stress stimulus.

In conclusion, the compared results of both tests showed that the endothelial cells 58 cultured on the membrane 6 of the first culture chamber 2 and subjected to shear stress stimulus:

a) maintain the confluence established prior to initiating the shear stress and show a correct cell morphology drawn out in the direction of application of the shear stress, which was not observed in the cells cultured under static conditions.

b) produce amounts of nitric oxide notably superior to the cells cultured under static conditions.

This last data b) is particularly relevant since it shows that the shear stress generated in the bioreactor 1 of the invention has protective characteristics for correctly stimulating the endothelial cells. As the skilled person knows, the nitric oxide of endothelial origin is only generated under shear stress of protective characteristics.

Furthermore, the analysis of the phenotype of the hepatic stellate cells 60 cultured in the second culture chamber 4 showed that the improvement of the phenotype of the endothelial cells 58 due to the shear stress paracrinally influences the hepatic stellate cells 60 which move on to a more healthy state.

As may be gathered from the known state of the art, up to now the improvement in the phenotype of the hepatic stellate cells 60 had only been proven through the improvement of the viability of the endothelial cells 58 with drugs. Therefore, the test carried out in the bioreactor 1 of the invention shows that the endothelial protection derived from the shear stress stimulus also paracrinally improves the phenotype of the hepatic stellate cells 60. Up to now, this evidence had not been described in the art, most probably due to the lack of a cell co-culture bioreactor under homogenous and controlled shear stress stimulus like that of the invention.

In parallel, the correct co-culture of other cell types which can interact with the endothelial cells 58 seeded on the membrane 6 has been proven. To be precise, an excellent adherence and viability of hepatocytes (liver parenchymal cells) has been proven.

The invention claimed is:

1. A bioreactor for cell co-culture, comprising:
   a base;
   a cover;
   a membrane between the base and the cover; and
   at least first and second cell culture chambers, said first chamber being provided between the membrane and the cover and the second membrane being provided between the membrane and the base,
   wherein said bioreactor can be disassembled by separating said base from said cover,
   wherein said membrane includes at least a first sealing gasket integrated with said membrane, and is porous for cell seeding and culturing,
   wherein said first sealing gasket is made of an elastomeric material and defines a closed perimeter delimiting an area of said membrane which is a first cell seed and culture area,
   wherein said first chamber includes at least one perfusion fluid inlet duct discharging a perfusion fluid into a first flow manifold and at least one outlet duct extending from a second flow manifold, wherein said first and second flow manifolds are provided at opposite ends of said first chamber and configured to discharge over said membrane the perfusion fluid across an entire width of said first chamber such that, in an assembled state of the bioreactor, a space is defined between the first cell seed and culture area of said membrane and a bottom of said first chamber, and wherein at least the bottom of said first chamber is dimensioned to cause a laminar flow of said perfusion fluid, said laminar flow having a homogenous velocity over a whole of said first cell seed and culture area.

2. The bioreactor of claim 1, wherein said membrane is a plurality of separate, mutually parallel membranes assembled in said bioreactor, to form additional cell culture chambers.

3. The bioreactor of claim 1, wherein said first and second flow manifolds are first and second longitudinal grooves that are deeper than said space.

4. The bioreactor of claim 1, wherein said space is between a first face of said membrane and said bottom of said first chamber and provides a shear stress effect on said membrane equivalent to values caused by blood stream flow in blood vessels of a human body.

5. The bioreactor of claim 4, wherein said shear stress effect is between 0.1 and 20 $N/m^2$.

6. The bioreactor of claim 1, wherein said membrane further comprises a second sealing gasket integral with said membrane and said second sealing gasket defines a closed perimeter delimiting a second cell seed and culture area of said membrane.

7. The bioreactor of claim 1, further comprising a housing of transparent material in at least part of an area corresponding to said first and second chambers.

8. The bioreactor of claim 1, further comprising a support arranged under said membrane so that said membrane rests, at least in part, on said support.

9. The bioreactor of claim 8, wherein said support is a grid.

10. The bioreactor of claim 8, wherein said support is at least one support column provided in a center of said second chamber and having a height such that, in an assembled state of said bioreactor, said membrane rests on said at least one support column.

11. The bioreactor of claim 5, wherein said sheer stress effect is between 0.3 and 3 $N/m^2$.

* * * * *